(12) United States Patent
Kisa

(10) Patent No.: US 10,980,986 B2
(45) Date of Patent: Apr. 20, 2021

(54) BALLOON CATHETER AND BALLOON CATHETER MANUFACTURING METHOD

(71) Applicant: KANEKA CORPORATION, Osaka (JP)

(72) Inventor: Toshiya Kisa, Osaka (JP)

(73) Assignee: KANEKA CORPORATION, Osaka (JP)

( * ) Notice: Subject to any disclaimer, the term of this patent is extended or adjusted under 35 U.S.C. 154(b) by 73 days.

(21) Appl. No.: 16/164,110

(22) Filed: Oct. 18, 2018

(65) Prior Publication Data

US 2019/0046775 A1 Feb. 14, 2019

Related U.S. Application Data

(63) Continuation of application No. PCT/JP2017/015457, filed on Apr. 17, 2017.

(30) Foreign Application Priority Data

Apr. 20, 2016 (JP) .............................. JP2016-084616

(51) Int. Cl.
*A61M 25/10* (2013.01)

(52) U.S. Cl.
CPC ........ *A61M 25/1029* (2013.01); *A61M 25/10* (2013.01); *A61M 25/1034* (2013.01);
(Continued)

(58) Field of Classification Search
CPC .. A61M 2025/1031; A61M 2025/1075; A61M 2025/1088; A61M 2205/0222;
(Continued)

(56) References Cited

U.S. PATENT DOCUMENTS

| 2004/0087901 A1* | 5/2004 | Rice ...................... A61L 29/085 604/96.01 |
| 2013/0261548 A1 | 10/2013 | Aggerholm et al. |
| 2014/0277071 A1 | 9/2014 | Wu et al. |

FOREIGN PATENT DOCUMENTS

| JP | H06-169995 A | 6/1994 |
| JP | H10-507088 A | 7/1998 |
| JP | 2004-305768 A | 11/2004 |

OTHER PUBLICATIONS

International Search Report issued in International Application No. PCT/JP2017/015457, dated Jul. 18, 2017 (1 page).
(Continued)

*Primary Examiner* — Deanna K Hall
(74) *Attorney, Agent, or Firm* — Osha Bergman Watanabe & Burton LLP

(57) ABSTRACT

A balloon catheter includes a shaft extending in one direction; a balloon disposed on the shaft; a first lubrication region; and a second lubrication region. The balloon in an expanded state includes a straight pipe portion; a first tapered portion disposed at a first end of the straight pipe portion in a long axis direction of the shaft; and a second tapered portion disposed at a second end of the straight pipe portion positioned opposite to the first end of the straight pipe portion in the long axis direction. Each of the first tapered portion and the second tapered portion tapers away from the straight pipe portion, and the first lubrication region extends over the straight pipe portion and the first tapered portion.

7 Claims, 9 Drawing Sheets

(52) U.S. Cl.
CPC .............. *A61M 2025/1031* (2013.01); *A61M 2025/1075* (2013.01); *A61M 2025/1088* (2013.01); *A61M 2205/0222* (2013.01); *A61M 2205/0238* (2013.01)

(58) Field of Classification Search
CPC .......... A61M 2205/0238; A61M 25/10; A61M 25/1029; A61M 25/1034
See application file for complete search history.

(56) References Cited

OTHER PUBLICATIONS

International Preliminary Report on Patentability issued in International Application No. PCT/JP2017/015457, dated Nov. 1, 2018 (6 pages).

* cited by examiner

BALLOON CATHETER AND BALLOON CATHETER MANUFACTURING METHOD

TECHNICAL FIELD

One or more embodiments of the present invention relate to a balloon catheter and a balloon catheter manufacturing method.

BACKGROUND

The technique that is described in Patent Literature 1 is known as a balloon catheter. The balloon catheter described in Patent Literature 1 comprises a shaft extending in one direction and a balloon disposed at a tip of the shaft. According to Patent Literature 1, the balloon has a straight tubular non-lubrication site (straight pipe portion) and tapered lubrication sites (tapered portions) at both ends thereof so that the insertability of the catheter inserted into a blood vessel is improved and slip of the balloon is prevented when the balloon is used, that is, when the blood vessel is occluded or expanded with the balloon. The balloon as described above is manufactured by a polymer material without surface lubricity constituting a balloon base material (balloon main body) and only the tapered parts being coated with a polymer material that has balloon base material surface lubricity.

CITATION LIST

Patent Literature

Patent Literature 1: Japanese Unexamined Patent Publication No. H6-169995

SUMMARY

In some cases, slip occurs during the use of the balloon even when only the tapered portions are given lubricity higher than the lubricity of the outer surface of the straight pipe portion as in the balloon described in Patent Literature 1.

One or more embodiments of the present invention provide a balloon catheter in which the slip resistance of a balloon can be improved and a balloon catheter manufacturing method.

One or more embodiments of the present invention relate to a balloon catheter in which a balloon is disposed on a shaft extending in one direction. The balloon in an expanded state during use of the balloon includes a straight pipe portion, a first tapered portion disposed at a first end of the straight pipe portion in a long axis direction of the shaft, and a second tapered portion disposed at a second end of the straight pipe portion positioned opposite to the first end of the straight pipe portion in the long axis direction. Each of the first tapered portion and the second tapered portion tapers away from the straight pipe portion, a low lubrication region ("first lubrication region") is provided over the straight pipe portion and at least one of the first tapered portion and the second tapered portion, at least a part of the low lubrication region is an annular-surface low lubrication region, and a surface high lubrication region ("second lubrication region") is provided adjacent to the low lubrication region in predetermined tapered portion corresponding to at least one of the first tapered portion and the second tapered portion and being provided with the low lubrication region.

In the balloon catheter described above, the balloon is attached to the shaft, and thus a tubular body such as a blood vessel can be occluded or expanded by expanding the balloon in the tubular body through which a liquid (such as blood) flows. The balloon has the high lubrication region in the predetermined tapered portion, and thus, for example, the balloon catheter is easily inserted into the tubular body. Furthermore, the low lubrication region is provided over the straight pipe portion and the predetermined tapered portion, and thus, for example, slip of the balloon with respect to the tubular body can be suppressed when the tubular body is occluded or expanded by expanding the balloon in the tubular body. In other words, slip resistance can be improved in the balloon catheter described above.

A coating higher in lubricity than the low lubrication region may constitute an outer surface of the high lubrication region, and a thickness of the low lubrication region may be less than a thickness of the high lubrication region in a state where the coating is swollen. In this case, the liquid between the straight pipe portion and the inner wall surface of the tubular body flows via the low lubrication region provided from the straight pipe portion to the predetermined tapered portion during expansion of the balloon even in a case where, for example, the tubular body is occluded or expanded by expanding the balloon in the tubular body. Accordingly, the straight pipe portion and the tubular body come into contact with each other with greater ease. Therefore, the anti-slip properties of the balloon catheter can be further improved.

An entire outer surface of the straight pipe portion may be the low lubrication region. As a result, the area of contact between the tubular body and the low lubrication region in the straight pipe portion can be increased when, for example, the tubular body is occluded or expanded with the balloon. Accordingly, slip of the balloon can be further suppressed.

The low lubrication region may be an annular-surface low lubrication region in the predetermined tapered portion.

The low lubrication region may be provided in the first tapered portion, a boundary between the high lubrication region and the low lubrication region provided in the first tapered portion may be orthogonal to the long axis direction in the lateral view of the balloon, and L2/L1 may be 0.05 to 0.9 when L1 is a length of the first tapered portion and L2 is a length of the low lubrication region provided in the first tapered portion in the long axis direction. In addition, the low lubrication region may be provided in the second tapered portion, a boundary between the high lubrication region and the low lubrication region provided in the second tapered portion may be orthogonal to the long axis direction in the lateral view of the balloon, and L4/L3 may be 0.05 to 0.9 when L3 is a length of the second tapered portion and L4 is a length of the low lubrication region provided in the second tapered portion in the long axis direction.

The low lubrication region may be an annular-surface low lubrication region to obliquely extend over the first tapered portion, the straight pipe portion and the second tapered portion in the lateral view of the balloon, and the high lubrication region may be the surface high lubrication region on both sides of the low lubrication region.

One or more embodiments of the present invention relate to a method for manufacturing a balloon catheter including a shaft extending in one direction and a balloon disposed on the shaft, the balloon, in an expanded state during use, having a first tapered portion, a second tapered portion, and a straight pipe portion positioned between the first tapered portion and the second tapered portion in a long axis direction of the shaft and each of the first tapered portion and the second tapered portion tapering away from the straight pipe portion. The method includes a step of attaching a balloon main body to the shaft, the balloon main body having a first region, a second region, and a third region corresponding to the straight pipe portion, the first tapered portion, and the second tapered portion respectively and a step of obtaining the balloon by forming, in the balloon main body, a coating higher in lubricity than the balloon main body. The coating is formed on at least one of the second region and the third region in the step of obtaining the balloon such that a low lubrication region is formed over the straight pipe portion and at least one of the first tapered portion and the second tapered portion, at least a part of the low lubrication region is an annular-surface low lubrication region, and a surface high lubrication region is formed adjacent to the low lubrication region in a predetermined tapered portion corresponding to at least one of the first tapered portion and the second tapered portion and being formed with the low lubrication region.

An example of the balloon catheter according to one or more embodiments of the present invention can be manufactured by the manufacturing method described above. Accordingly, a slip resistance-improved balloon catheter can be provided by the manufacturing method.

The step of obtaining the balloon may include an arrangement step of arranging the balloon main body in a straight tubular masking member such that the first region is positioned in the masking member having an outer diameter of the straight pipe portion as an inner diameter in the expanded state during use of the balloon, longer in length than the first region, and shorter in length than the balloon main body, an expansion step of expanding the balloon main body such that parts of regions in the second region and the third region masked with the masking member are exposed from the masking member with the balloon main body arranged in the masking member in the arrangement step, and a lubrication step of providing lubricity for the balloon main body by forming the coating in a region of the balloon main body exposed from the masking member after the balloon main body is expanded in the expansion step.

In this case, the inner diameter of the masking member is equal to the outer diameter of the straight pipe portion in the expanded state during use of the balloon, when the balloon main body is expanded in the expansion step, and thus the balloon main body does not expand in a radial direction after the first region comes into contact with the inner surface of the masking member. Accordingly, the balloon main body extends in the axial direction of the masking member. Therefore, parts of the regions of the second region and the third region masked with the masking member in the arrangement step are exposed from the masking member in the expansion step with the first region remaining masked with the masking member. As a result, forming the coating in the lubrication step in the region of the balloon main body exposed from the masking member makes it possible to form the coating on a part of the second region and a part of the third region without forming a coating on the first region. Therefore, an embodiment, in which the masking member is used, makes it possible to manufacture a balloon catheter in which no coating is formed in the straight pipe portion and the coating is formed on the sides of the first tapered portion and the second tapered portion opposite to the straight pipe portion.

According to one or more embodiments of the present invention, a balloon catheter in which the slip resistance of a balloon can be improved and a balloon catheter manufacturing method can be provided.

DESCRIPTION OF EMBODIMENTS

Figure 1:
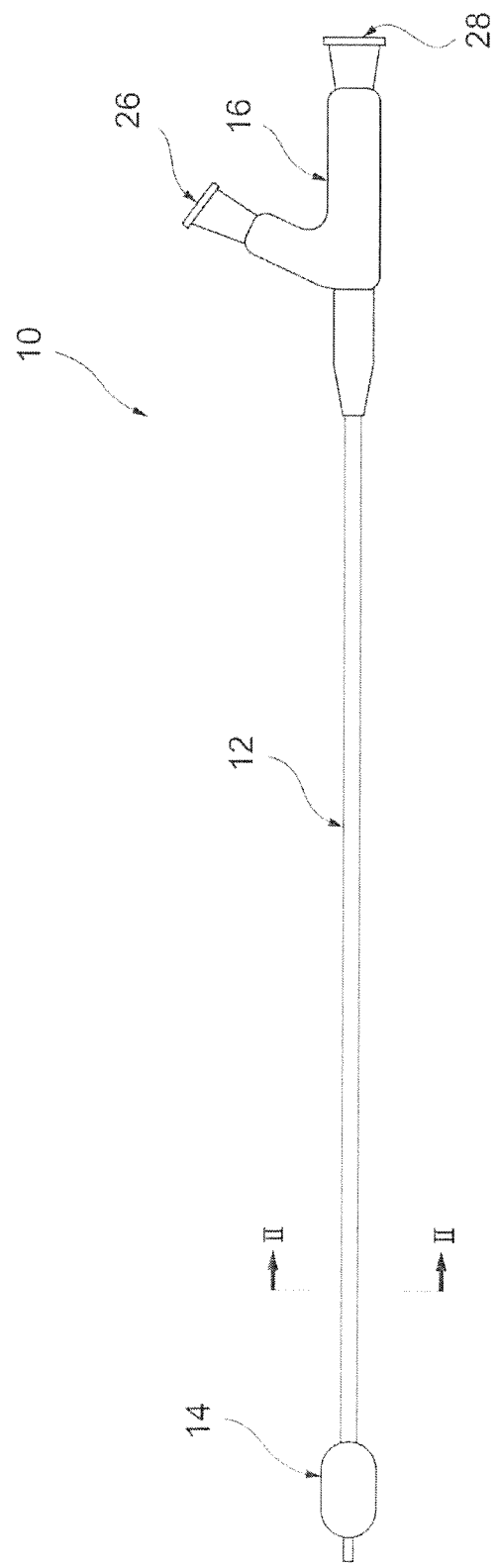
FIG. 1 is a drawing illustrating a schematic configuration of a balloon catheter according to one embodiment.

Hereinafter, one or more embodiments of the present invention will be described with reference to accompanying drawings. The same reference numerals will be used to refer to the same elements so that description is not repeated. The dimension ratios of the drawings do not necessarily correspond to the description.

As schematically illustrated in FIGS. 1 to 4, a balloon catheter 10 has a shaft with coating 12, and a balloon 14. The balloon catheter 10 is a catheter for blood vessel occluding that occludes a blood vessel by expanding the balloon 14 in the blood vessel. An expanded state during use of the balloon 14 is illustrated in FIGS. 1 to 4. In this specification, the "expanded state during use" means a state where the balloon is expanded within a range of elastic deformation. The range of elastic deformation means a range in which a shape substantially similar to the shape of the balloon 14 while expanded can be maintained even when expansion and contraction of the balloon 14 are repeated.

A manifold 16 may be bonded to one end of the shaft with coating 12. In the present embodiment, an embodiment provided with the manifold 16 will be described. In this specification, "distal" and "proximal" are terms with respect to the end of the shaft with coating 12 on the manifold 16 side, that is, the end of the balloon catheter 10 on an operator side, unless otherwise noted.

Figure 2:
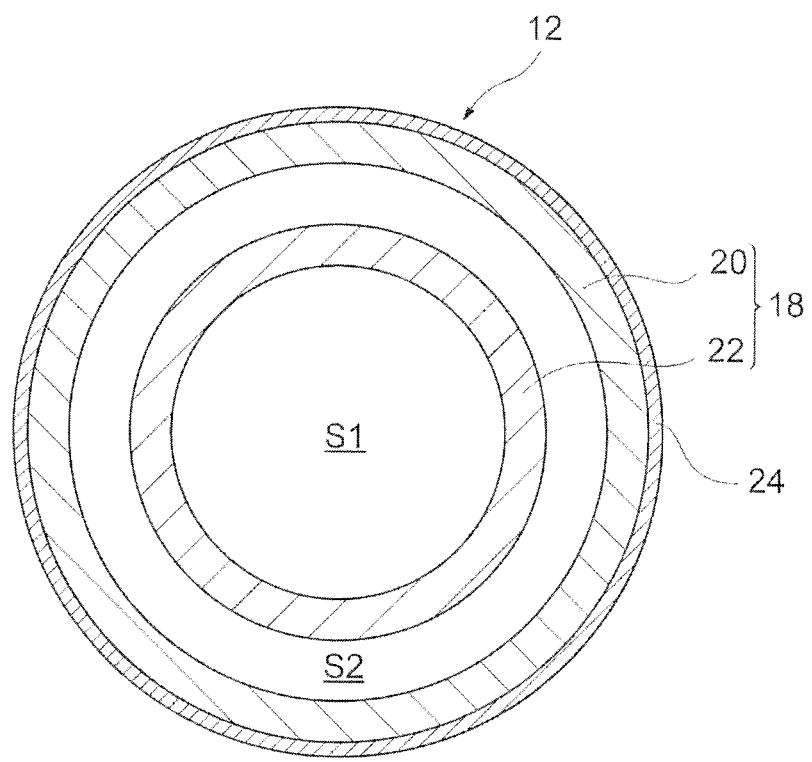
FIG. 2 is a sectional view taken along line II-II of FIG. 1.

The shaft with coating 12 has a shaft 18 extending in one direction. As illustrated in FIG. 2, the shaft 18 has a double pipe structure in which an inner shaft 22 is arranged concentrically with an outer shaft 20. However, the configuration of the shaft 18 is not limited as long as the shaft 18 has one main lumen (described later) and one inflation lumen (described later).

The outer shaft 20 and the inner shaft 22 may be constituted by known materials. Examples of the materials of the outer shaft 20 and the inner shaft 22 include polyolefin, polyolefin elastomer, polyester, polyester elastomer, polyamide, polyamide elastomer, polyurethane, and polyurethane elastomer.

As schematically illustrated in FIG. 2, the shapes of the outer shaft 20 and the inner shaft 22 are circular (for example) in the cross section of the shaft 18, that is, the section of the shaft 18 that is orthogonal to the direction of a long axis C (hereinafter, also referred to as a "long axis direction C" in some cases). The shapes may also be elliptical. A space S1 defined by the inner surface of the inner shaft 22 functions as the main lumen for passing a drug, a guide wire, and so on. A space S2 between the inner shaft 22 and the outer shaft 20 communicates with the balloon 14 and functions as the inflation lumen for passing a medium for expanding the balloon 14 (such as a physiological salt solution, a contrast agent, and a mixture thereof).

Figure 3:
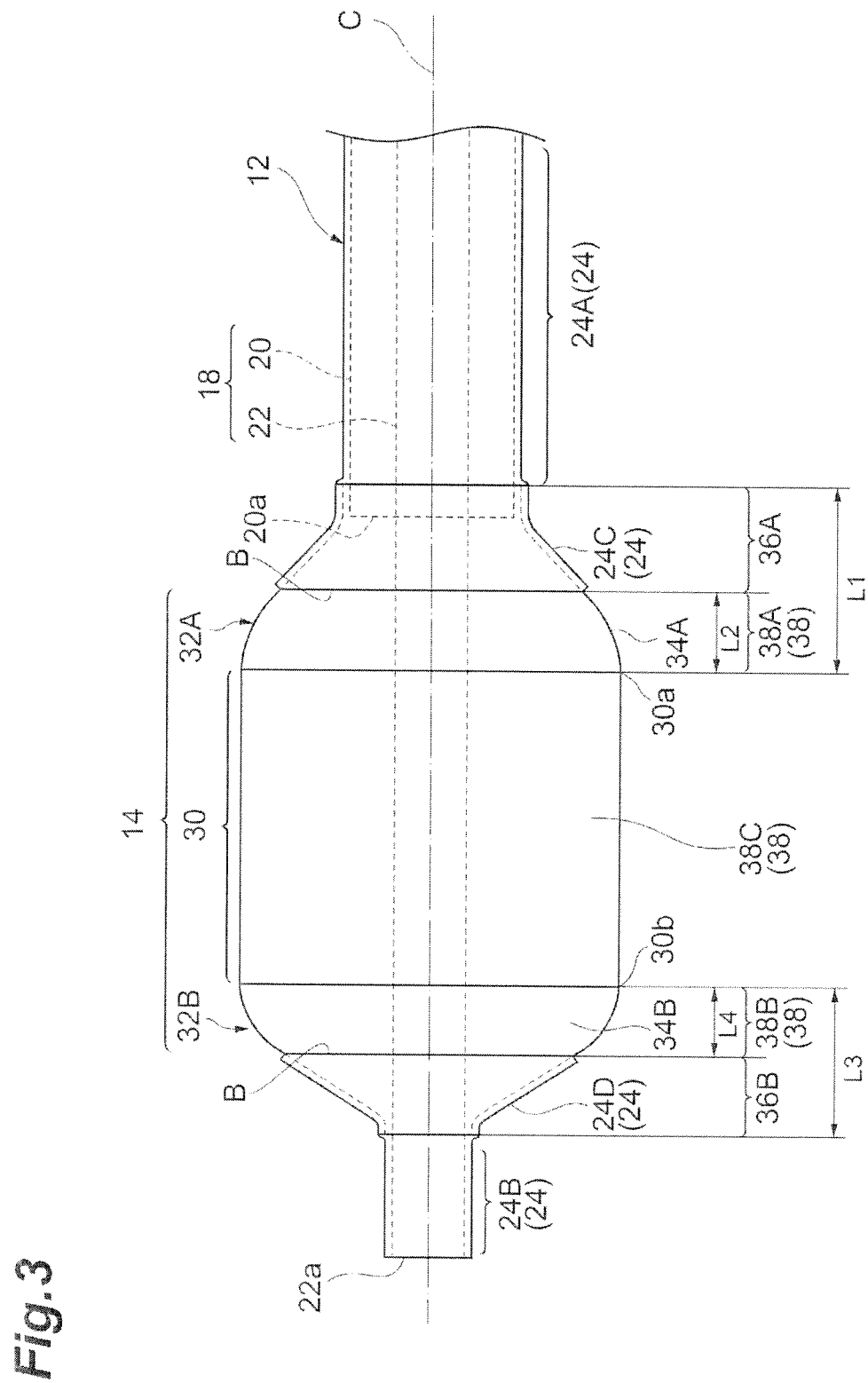
FIG. 3 is an enlarged view of the vicinity of a balloon of the balloon catheter illustrated in FIG. 1.
Figure 4:
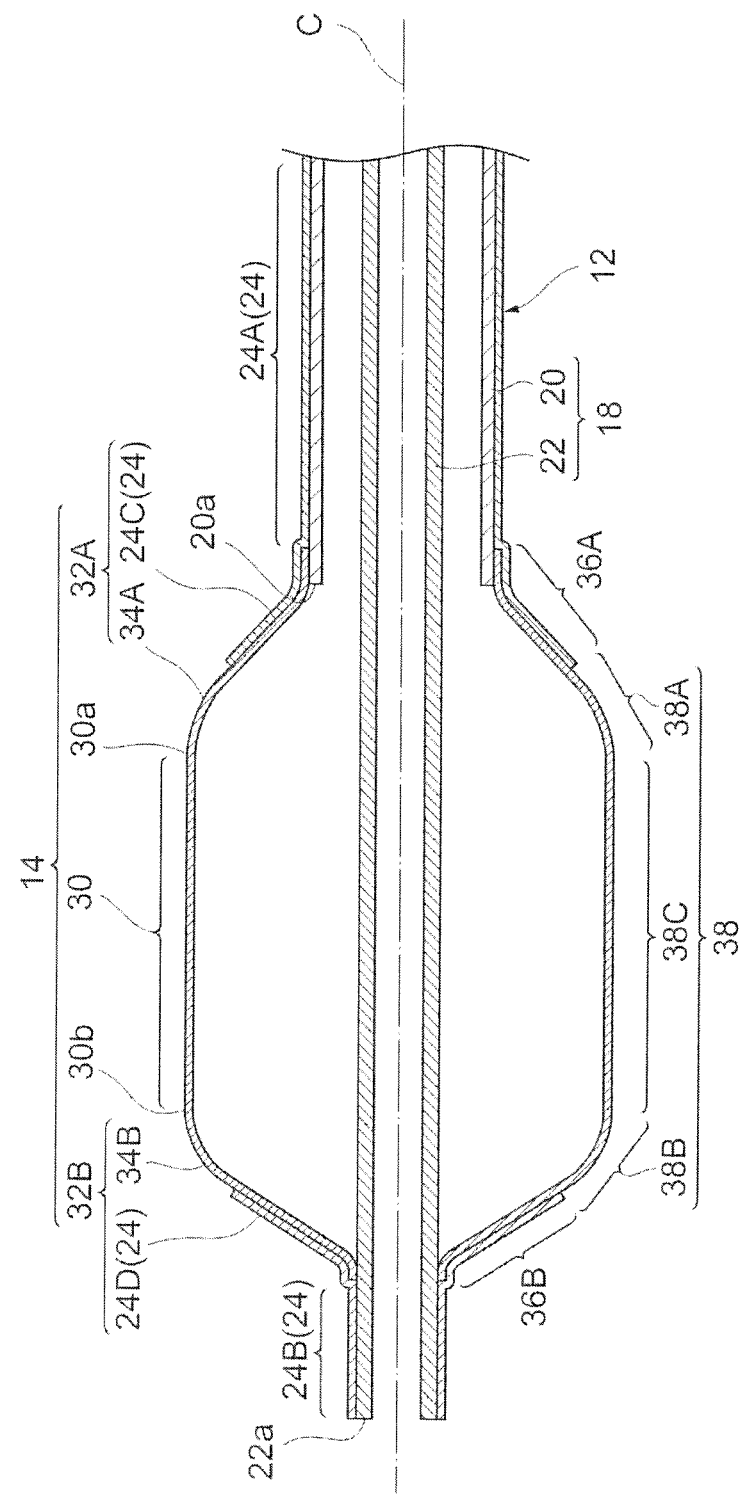
FIG. 4 is longitudinal sectional view of the shaft and the balloon illustrated in FIG. 3.

As illustrated in FIGS. 3 and 4, the vicinity of a distal end 22a of the inner shaft 22 protrudes from a distal end 20a of the outer shaft 20, and the part of the inner shaft 22 exposed from the outer shaft 20 penetrates the balloon 14.

The shaft with coating 12 is coated with a hydrophilic coating 24. Specifically, the outer shaft 20 and the part of the inner shaft 22 protruding from the balloon 14 (that is, the vicinity of the distal end of the inner shaft 22) are coated with the hydrophilic coating 24. As a result, the shaft with coating 12 slides easily. For convenience of description, the region of the hydrophilic coating 24 with which the outer shaft 20 is coated may be referred to as a hydrophilic coating 24A, and the region of the hydrophilic coating 24 with which the part of the inner shaft 22 protruding from the balloon 14 in the long axis direction C is coated may be referred to as a hydrophilic coating 24B. As described later, a part of the balloon 14 is also coated with the hydrophilic coating 24.

Examples of the material of the hydrophilic coating 24 include a hydrophilic polymer such as polyethylene glycol, polyacrylamide, polyvinylpyrrolidone, and a methyl vinyl ether-maleic anhydride copolymer. The thickness of the hydrophilic coating 24 may be set in accordance with the thickness of the region of the hydrophilic coating 24 provided on the balloon 14.

The proximal end of the balloon 14 is bonded to the vicinity of the distal end 20a of the outer shaft 20 and the distal end of the balloon 14 is bonded to the inner shaft 22. As a result, the inside of the balloon 14 communicates with the space S2 (refer to FIG. 2) between the inner shaft 22 and the outer shaft 20. Methods for bonding the balloon 14 to the outer shaft 20 and the inner shaft 22 are not limited as long as the methods are usually used for balloon catheters. For example, the bonding may be adhesive bonding or thermal welding.

As illustrated in FIG. 1, the manifold 16 is bonded to one end of the shaft with coating 12 (specifically, the shaft 18). Methods for bonding the manifold 16 to the shaft with coating 12 are not limited as long as the methods are usually used for balloon catheters. For example, the bonding may be adhesive bonding or thermal welding.

An expansion medium input and output portion 26 and a treatment portion 28 are provided on the manifold 16. The expansion medium input and output portion 26 has a lumen which communicates with the inflation lumen (space S2 in FIG. 2) and through which passes a medium for expanding the balloon 14. The treatment portion 28 has a lumen which communicates with the main lumen (space S1 in FIG. 2) and through which passes the drug, the guide wire and so on to the main lumen.

The balloon 14 will be described in detail below.

The balloon 14 is a hollow body as illustrated in FIGS. 3 and 4. In the expanded state during use of the balloon 14, the balloon 14 has a straight pipe portion 30, a proximal tapered portion (first tapered portion) 32A and a distal tapered portion (second tapered portion) 32B, and is disposed on the shaft 18. Hereinafter, the balloon 14 will be described based on the expanded state of the balloon 14, unless otherwise noted.

The straight pipe portion 30 extends in the long axis direction C of the shaft 18. The length of the straight pipe portion 30 is, for example, 2 mm to 15 mm. The length of the straight pipe portion 30 may be 4 mm to 8 mm. Examples of the material of the straight pipe portion 30 include polyolefin, polyolefin elastomer, polyester, polyester elastomer, polyamide, polyamide elastomer, polyurethane, and polyurethane elastomer. The lubricity of the material of the straight pipe portion 30 may be lower than the lubricity of the hydrophilic coating 24.

The straight pipe portion 30 is a contact region coming into contact with the inner wall surface of a blood vessel when the blood vessel is occluded with the balloon 14 (when the balloon 14 is used). A diameter may be selected for the straight pipe portion 30 such that the blood vessel can be occluded in accordance with the size of the blood vessel in which the balloon 14 is used. The outer diameter of the straight pipe portion 30 is, for example, 1 mm to 10 mm. The outer diameter of the straight pipe portion 30 may be 2 mm to 6 mm. The straight pipe portion 30 may be formed with a thin wall.

The proximal tapered portion 32A is disposed at a proximal end (first end) 30a of the straight pipe portion 30. The proximal tapered portion 32A tapers away from the straight pipe portion 30, and the proximal end of the proximal tapered portion 32A (that is, the end on the manifold 16 side) is bonded to the vicinity of the distal end 20a of the outer shaft 20. Accordingly, the proximal tapered portion 32A has a tapered shape, tapering from the straight pipe portion 30 toward the distal end of the outer shaft 20.

The proximal tapered portion 32A may be a non-contact region that does not come into contact with a blood vessel when the balloon 14 is used. L1 is, for example, 1 mm to 5 mm when L1 is the length of the proximal tapered portion 32A in the long axis direction C.

The proximal tapered portion 32A is configured such that the hydrophilic coating 24 is provided on a proximal tapered portion main body 34A. The shape of the proximal tapered portion main body 34A is substantially similar to the shape of the proximal tapered portion 32A. For convenience of description, the part of the hydrophilic coating 24 with which the proximal tapered portion main body 34A is coated will also be referred to as a hydrophilic coating 24C.

The proximal tapered portion main body 34A can be formed with a thin wall as is the case with the straight pipe portion 30. Examples of the material of the proximal tapered portion main body 34A are similar to the examples of the material of the straight pipe portion 30. In the present embodiment, the material of the proximal tapered portion main body 34A is the same as the material of the straight pipe portion 30. In this case, the proximal tapered portion main body 34A can be molded integrally with the straight pipe portion 30.

A part of the outer surface of the proximal tapered portion main body 34A is surface coated with the hydrophilic coating 24C. Specifically, the outer surface of the proximal tapered portion main body 34A is surface coated with the hydrophilic coating 24C in a circumferential direction such that an annular-surface uncoated region is left in the vicinity of the distal end of the proximal tapered portion main body 34A (end on the straight pipe portion 30 side). Accordingly, there is one boundary B between the region of the proximal tapered portion 32A coated with the hydrophilic coating 24C and the uncoated region, and this boundary B makes a circle in the circumferential direction of the proximal tapered portion 32A. Therefore, the long axis direction C and the boundary B intersect with each other (are orthogonal to each other in the present embodiment) in the lateral view of the balloon 14. In other words, when the boundary B is projected onto a virtual plane including the long axis C, the long axis C and the projected boundary B intersect with each other.

The region of the proximal tapered portion 32A that is coated with the hydrophilic coating 24C is higher in lubricity (that is, slidability) than the region of the proximal tapered portion 32A that is not coated with the hydrophilic coating 24C. Accordingly, the region of the proximal tapered portion 32A that is coated with the hydrophilic coating 24C will be referred to as a high lubrication region 36A and the region of the proximal tapered portion 32A that is not coated with the hydrophilic coating 24C will be referred to as a low lubrication region 38A. In this configuration, the outer surface of the high lubrication region 36A is the outer surface of the hydrophilic coating 24C and the outer surface of the low lubrication region 38A is the outer surface of the proximal tapered portion main body 34A.

It is enough that the thickness of the hydrophilic coating 24C and the position of the boundary B are set such that the hydrophilic coating 24C does not come into contact with the inner wall surface of a blood vessel when the balloon 14 is expanded during use of the balloon 14. The hydrophilic coating 24C is provided such that the thickness of the hydrophilic coating 24C may be, for example, 1 μm to 100 μm or 3 μm to 30 μm when the hydrophilic coating 24C is swollen by five-minute soaking in a physiological salt solution. As illustrated in FIG. 3, in an embodiment in which the boundary B is orthogonal to the long axis direction C, L2 can be set such that, for example, L2/L1 is 0.05 to 0.9 or 0.2 to 0.5 when L2 is the length of the low lubrication region 38A in the long axis direction C of the shaft 18. As described above, L1 is the length of the proximal tapered portion 32A in the long axis direction C of the shaft 18.

The distal tapered portion 32B is disposed at a distal end (second end) 30b of the straight pipe portion 30 on the side opposite to the proximal end 30a. The distal tapered portion 32B tapers away from the straight pipe portion 30, and the distal end of the distal tapered portion 32B (that is, the end on the distal end 22a side of the inner shaft 22) is bonded to the inner shaft 22. Accordingly, the distal tapered portion 32B has a tapered shape, tapering from the straight pipe portion 30 toward the distal end 22a of the inner shaft 22.

The distal tapered portion 32B may be a non-contact region that does not come into contact with a blood vessel when the balloon 14 is used as is the case with the proximal tapered portion 32A. L3 is, for example, 1 mm to 5 mm when L3 is the length of the distal tapered portion 32B in the long axis direction C.

The distal tapered portion 32B is configured such that the hydrophilic coating 24 is provided on a distal tapered portion main body 34B. The shape of the distal tapered portion main body 34B is substantially similar to the shape of the distal tapered portion 32B. For convenience of description, the part of the hydrophilic coating 24 with which the distal tapered portion main body 34B is coated may be referred to as a hydrophilic coating 24D.

The distal tapered portion main body 34B can be formed with a thin wall as is the case with the straight pipe portion 30. Examples of the material of the distal tapered portion main body 34B are similar to the examples of the material of the straight pipe portion 30. In the present embodiment, the material of the distal tapered portion main body 34B is the same as the material of the straight pipe portion 30. In this case, the distal tapered portion main body 34B can be molded integrally with the straight pipe portion 30.

A part of the outer surface of the distal tapered portion main body 34B is surface coated with the hydrophilic coating 24D disposed on the distal tapered portion 32B. Specifically, the outer surface of the distal tapered portion main body 34B is surface coated with the hydrophilic coating 24D in a circumferential direction such that an annular-surface uncoated region is left in the vicinity of the proximal end of the distal tapered portion main body 34B (end on the straight pipe portion 30 side). Accordingly, there is one boundary B between the region of the distal tapered portion 32B coated with the hydrophilic coating 24D and the uncoated region, and this boundary B makes a circle in the circumferential direction of the distal tapered portion 32B. Therefore, the long axis direction C and the boundary B in the distal tapered portion 32B intersect with each other (are orthogonal to each other in the present embodiment) in the lateral view of the balloon 14. In other words, when the boundary B on the distal tapered portion 32B is projected onto a virtual plane including the long axis C, the long axis C and the projected boundary B intersect with each other.

The region of the distal tapered portion 32B that is coated with the hydrophilic coating 24D is higher in lubricity (that is, slidability) than the region of the distal tapered portion 32B that is not coated with the hydrophilic coating 24D. Accordingly, the region of the distal tapered portion 32B that is coated with the hydrophilic coating 24D will be referred to as a high lubrication region 36B and the region of the distal tapered portion 32B that is not coated with the hydrophilic coating 24D will be referred to as a low lubrication region 38B. In this configuration, the outer surface of the high lubrication region 36B is the outer surface of the hydrophilic coating 24D and the outer surface of the low lubrication region 38B is the outer surface of the distal tapered portion main body 34B.

The thickness of the hydrophilic coating 24D and the position of the boundary B in the distal tapered portion 32B may be set such that the hydrophilic coating 24D does not come into contact with the inner wall surface of a blood vessel when the balloon 14 is expanded during use of the balloon 14. The thickness of the hydrophilic coating 24D is similar to the example of the thickness of the hydrophilic coating 24C. As illustrated in FIG. 3, in an embodiment in which the boundary B is orthogonal to the long axis direction C, L4 can be set such that, for example, L4/L3 is 0.05 to 0.9 or 0.2 to 0.5 when L4 is the length of the low lubrication region 38B in the long axis direction C of the shaft 18. As described above, L3 is the length of the distal tapered portion 32B in the long axis direction C of the shaft 18.

In the balloon 14 configured as described above, the hydrophilic coating 24 is not provided on the straight pipe portion 30. Accordingly, the entire outer surface of the straight pipe portion 30 is a low lubrication region 38C that is lower in lubricity than the high lubrication regions 36A and 36B. Therefore, the low lubrication region 38C is an annular-surface low lubrication region around the entire circumference of the straight pipe portion 30.

The high lubrication regions 36A and 36B in the balloon 14 have the hydrophilic coatings 24C and 24D. Accordingly, the thickness of the high lubrication region 36A is equal to the sum of the thickness of the proximal tapered portion main body 34A and the thickness of the hydrophilic coating 24C. The thickness of the high lubrication region 36B is equal to the sum of the thickness of the distal tapered portion main body 34B and the thickness of the hydrophilic coating 24D. The low lubrication regions 38A, 38B, and 38C do not have the hydrophilic coatings 24C and 24D. Accordingly, the thicknesses of the low lubrication regions 38A, 38B, and 38C are the thicknesses of the straight pipe portion 30, the proximal tapered portion main body 34A, and the distal tapered portion main body 34B respectively. Therefore, the thicknesses of the low lubrication regions 38A, 38B, and 38C are less than the thicknesses of the high lubrication regions 36A and 36B in a state where the shaft with coating 12 of the balloon catheter 10 is inserted into a blood vessel and the hydrophilic coatings 24C and 24D are swollen. A state where the hydrophilic coatings 24C and 24D are swollen in a blood vessel can correspond to a swollen state in a case where the hydrophilic coatings 24C and 24D are soaked in physiological salt solution (such as a case where the hydrophilic coatings 24C and 24D are soaked in physiological salt solution for five minutes). In an embodiment in which the thicknesses of the straight pipe portion 30, the proximal tapered portion main body 34A, and the distal tapered portion main body 34B are almost the same, the thicknesses of the low lubrication regions 38A, 38B, and 38C are less than the thicknesses of the high lubrication regions 36A and 36B even in a state where the hydrophilic coatings 24C and 24D are not swollen.

A method for manufacturing the balloon catheter 10 will be described below. For the purpose of description, the balloon 14 in a state where the hydrophilic coating 24 is not provided will be referred to as a balloon main body 40. In the present embodiment, the hydrophilic coating 24 is not provided on the straight pipe portion 30, and thus the straight pipe portion 30, the proximal tapered portion main body 34A, and the distal tapered portion main body 34B constitute the balloon main body 40. In other words, in the balloon main body 40, the proximal tapered portion main body 34A and the distal tapered portion main body 34B are regions that become the proximal tapered portion 32A and the distal tapered portion 32B by the formation of the hydrophilic coatings 24C and 24D.

When the balloon catheter 10 is manufactured, the shaft 18, which has the outer shaft 20 and the inner shaft 22 arranged therein, is bonded to the manifold 16, first. The balloon main body 40 is manufactured while the shaft 18 and the manifold 16 are bonded. The balloon main body 40 may be manufactured by a known method regarding balloon catheters. For example, the balloon main body 40 can be manufactured by extrusion molding using the material of the balloon main body 40 to form a tubular member, and applying a biaxial stretch blow molding method to the tubular member.

Subsequently, a step of attaching the balloon main body 40 to the shaft 18 is performed. The balloon main body 40 can be attached to the shaft 18 by the bonding methods known in balloon catheter-related technical fields, such as adhesive bonding and thermal welding as described above.

Next, a step of obtaining the balloon 14 by forming the hydrophilic coatings 24C and 24D on the balloon main body 40 and a step of obtaining the shaft with coating 12 by forming the hydrophilic coatings 24A and 24B on the shaft 18 are performed. The balloon catheter 10 can be manufactured as a result of the steps. In the present embodiment, the step of obtaining the balloon 14 and the step of obtaining the shaft with coating 12 are performed as the same step. Accordingly, the step of obtaining the balloon 14 will be described with reference to FIGS. 5 and 6.

First, the balloon main body 40 is concentrically and relatively inserted into a straight tubular masking member 42 such that the straight pipe portion (first region) 30 is positioned in the masking member 42 (arrangement step). In this stage, the balloon main body 40 can be in a folded state. The inner diameter of the masking member 42 is substantially equal to the outer diameter of the straight pipe portion 30 in the expanded state during use of the balloon main body 40. The length of the masking member 42 is longer than the length of the straight pipe portion 30 and shorter than the length of the balloon main body 40. Although the material of the masking member 42 is not limited, examples thereof include polyolefin, polyolefin elastomer, polyester, polyester elastomer, polyamide, polyamide elastomer, polyurethane, polyurethane elastomer, silicone, polytetrafluoroethylene, polypropylene, and polycarbonate.

The masking member 42 is longer than the straight pipe portion 30 and shorter than the balloon main body 40. Accordingly, in the arrangement state of the balloon main body 40 with respect to the masking member 42 in the arrangement step described above, the regions of the proximal tapered portion main body (second region) 34A and the distal tapered portion main body (third region) 34B on the straight pipe portion 30 side are positioned in the masking member 42 and the regions of the proximal tapered portion main body (second region) 34A and the distal tapered portion main body (third region) 34B on the bonding end sides with respect to the shaft 18 are exposed from the masking member 42.

Figure 5:
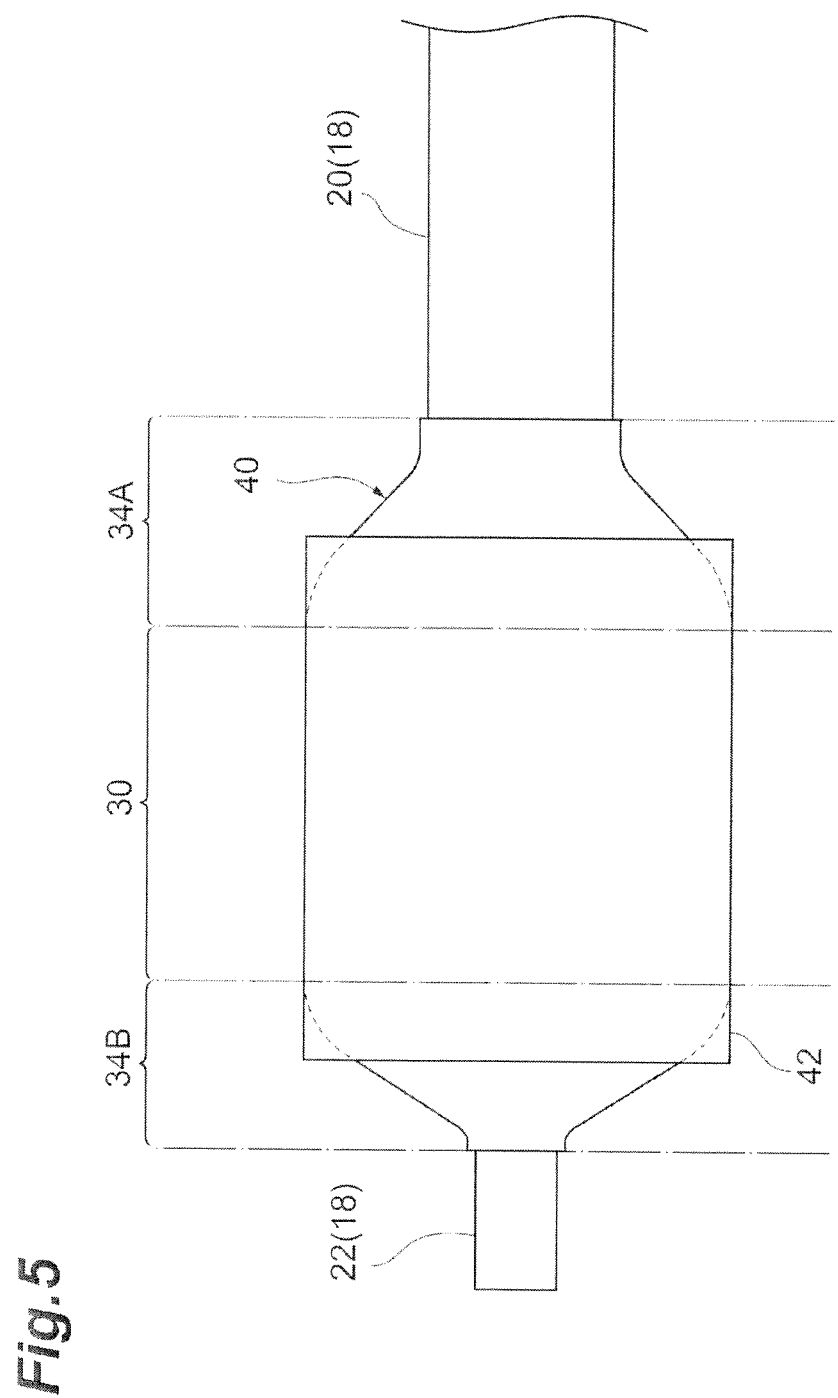
FIG. 5 is a drawing for describing a method for manufacturing the balloon catheter illustrated in FIG. 1.
Figure 6:
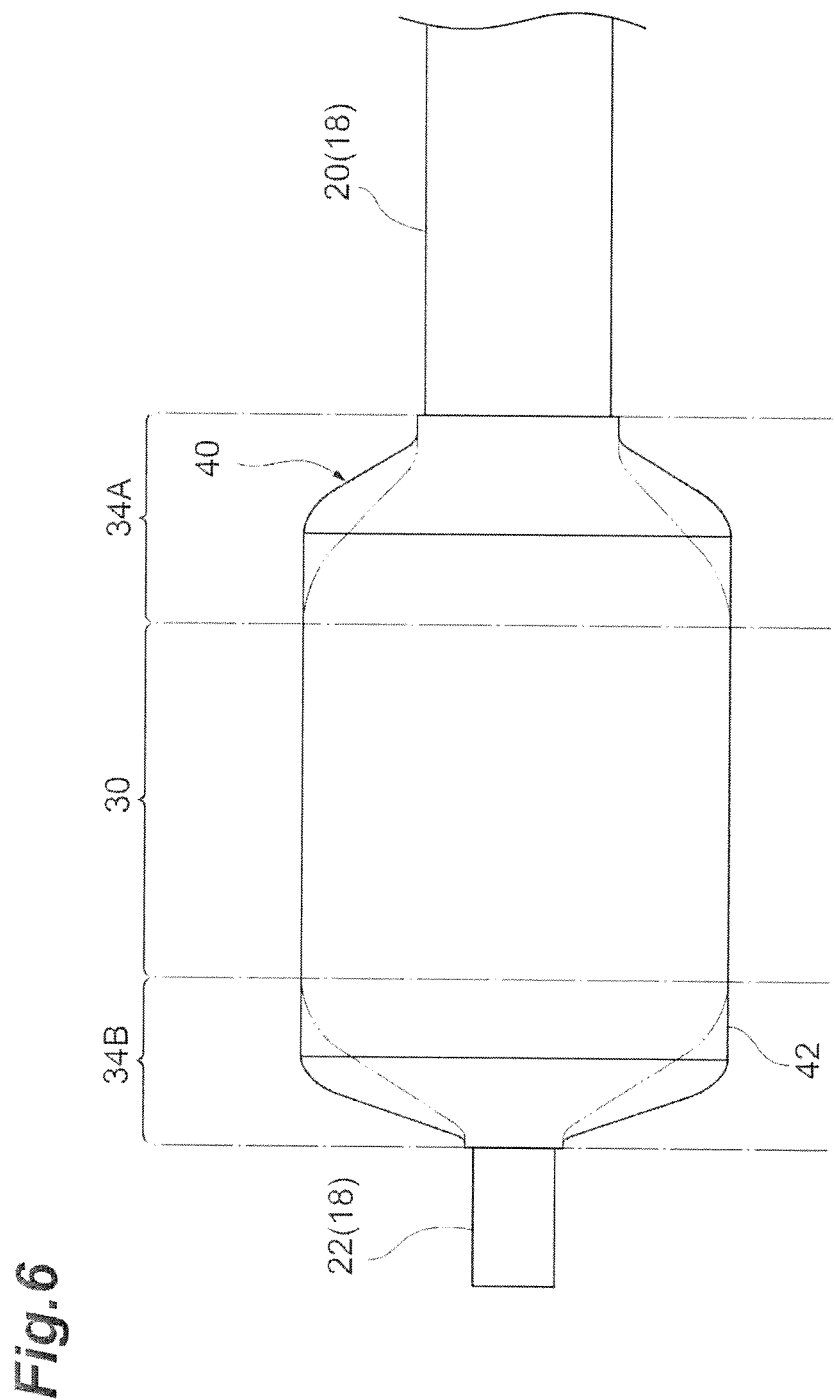
FIG. 6 is a drawing for describing a state where a balloon main body is further expanded from the state illustrated in FIG. 5 in the method for manufacturing the balloon catheter illustrated in FIG. 1.

Subsequently, as illustrated in FIG. 5, the balloon main body 40 is expanded to the extent that the outer surface of the straight pipe portion 30 comes into contact with the inner surface of the masking member 42 (first expansion step). Next, as illustrated in FIG. 6, the balloon main body 40 is further expanded from the state of FIG. 5 within the range of elastic deformation (second expansion step). In FIG. 6, the proximal tapered portion main body 34A and the distal tapered portion main body 34B in the state illustrated in FIG. 5 are indicated by two-dot chain lines. Expansion of the balloon main body 40 in the radial direction is prevented by the masking member 42. Accordingly, in the second expansion step, the balloon main body 40 extends in the axial direction of the balloon main body 40 (corresponding to the long axis direction C illustrated in FIGS. 3 and 4). As a result, parts of the regions of the proximal tapered portion main body 34A and the distal tapered portion main body 34B that are positioned in the masking member 42 in the state illustrated in FIG. 5 (regions masked with the masking member 42) are exposed to the outside of the masking member 42. Although the description of the expansion stage of the balloon main body 40 has been divided into the first expansion step and the second expansion step for convenience of description, the first expansion step and the second expansion step may also be continuously performed as a single step.

Next, lubricity is provided for the balloon main body 40 by performing hydrophilic coating on the region of the balloon main body 40, which is exposed from the masking member 42, to form the hydrophilic coating 24 (lubrication step).

The portion where the proximal tapered portion 32A and the straight pipe portion 30 are connected to each other and the portion where the distal tapered portion 32B and the straight pipe portion 30 are connected to each other are in contact with the inner surface of the masking member 42, and thus hardly move even when the balloon main body 40 is expanded from the state illustrated in FIG. 5. Accordingly, the part of the proximal tapered portion main body 34A on the straight pipe portion 30 side, the part of the distal tapered portion main body 34B on the straight pipe portion 30 side, and the straight pipe portion 30 are masked with the masking member 42, and thus the hydrophilic coating 24 is not formed there.

Accordingly, as described above with reference to FIGS. 3 and 4, the hydrophilic coating 24 is formed on the balloon main body 40 such that the proximal tapered portion main body 34A and the distal tapered portion main body 34B have the boundaries B. The balloon 14 is manufactured as a result. The hydrophilic coating 24 is formed by performing hydrophilic coating on the shaft 18 at the same time as performing hydrophilic coating on the balloon main body 40 as described above. As a result, the balloon catheter 10 having the balloon 14 and the shaft with coating 12 can be manufactured.

The length of the masking member 42 may be the sum of the length of the straight pipe portion 30 and the lengths L3 and L4 illustrated in FIG. 3, for example, in order to form the hydrophilic coating 24 on the balloon main body 40 such that the proximal tapered portion main body 34A and the distal tapered portion main body 34B have the boundaries B.

Although methods for forming the hydrophilic coating 24 are not limited, the hydrophilic coating 24 can be formed by, for example, applying a coating solution, which contains the material of the hydrophilic coating 24, to the region where the hydrophilic coating 24 is to be formed, and then drying the coating solution. Alternatively, the hydrophilic coating 24 may be formed by another method such as spray coating.

During treatment using the balloon catheter 10 described above, the shaft with coating 12 is inserted into a blood vessel in a state where the balloon 14 is folded. At that time, a guide wire is passed through the main lumen (space S1) and the distal end of the shaft with coating 12 is guided by the guide wire into the blood vessel to a target site (that is, a treatment site). When the distal end of the shaft with coating 12 reaches the target part, the balloon 14 is expanded via the inflation lumen (space S2) to occlude the blood vessel. At this time, therapeutic treatment is performed at the target site if necessary.

In the balloon catheter 10, the hydrophilic coating 24 is provided on a part of the proximal tapered portion 32A of the balloon 14, a part of the distal tapered portion 32B of the balloon 14 and the shaft 18, and thus the balloon catheter 10 can be smoothly inserted into a blood vessel.

The high lubrication regions 36A and 36B and the low lubrication regions 38A and 38B are provided in the proximal tapered portion 32A and the distal tapered portion 32B of the balloon 14 such that the boundaries B are on the proximal tapered portion 32A and the distal tapered portion 32B. Specifically, in the proximal tapered portion 32A and the distal tapered portion 32B, regions not coated with the hydrophilic coating 24 (22C and 22D) are provided in the entire circumferential direction on the straight pipe portion 30 side and regions coated with the hydrophilic coating 24 are provided in the entire circumferential direction on the sides opposite to the straight pipe portion 30 (bonding portion sides with respect to the shaft 18).

In addition, in the balloon 14, the hydrophilic coating 24 is not provided on the outer surface of the straight pipe portion 30. In other words, the entire outer surface of the straight pipe portion 30 (that is, the entire circumferential direction) is the low lubrication region 38C (refer to FIGS. 3 and 4) lower in lubricity than the region coated with the hydrophilic coating 24. Accordingly, the low lubrication region 38C of the straight pipe portion 30 is continuously connected to the low lubrication regions 38A and 38B of the proximal tapered portion 32A and the distal tapered portion 32B.

In other words, in the balloon 14, a low lubrication region divided into the low lubrication regions 38A, 38B, and 38C (hereinafter, also referred to as a "low lubrication region 38") is provided as an annular-surface low lubrication region over the straight pipe portion 30, the proximal tapered portion 32A, and the distal tapered portion 32B and the high lubrication regions 36A and 36B are annular-surface high lubrication regions on both sides of the low lubrication region 38.

As a result of the above-described configuration of the balloon 14, slip of the straight pipe portion 30 with respect to the inner wall surface of a blood vessel is more reliably suppressed when the blood vessel is occluded with the balloon 14. This will be described below in comparison to a case where the hydrophilic coating 24 is provided on the whole of proximal and distal tapered portions.

Figure 7:
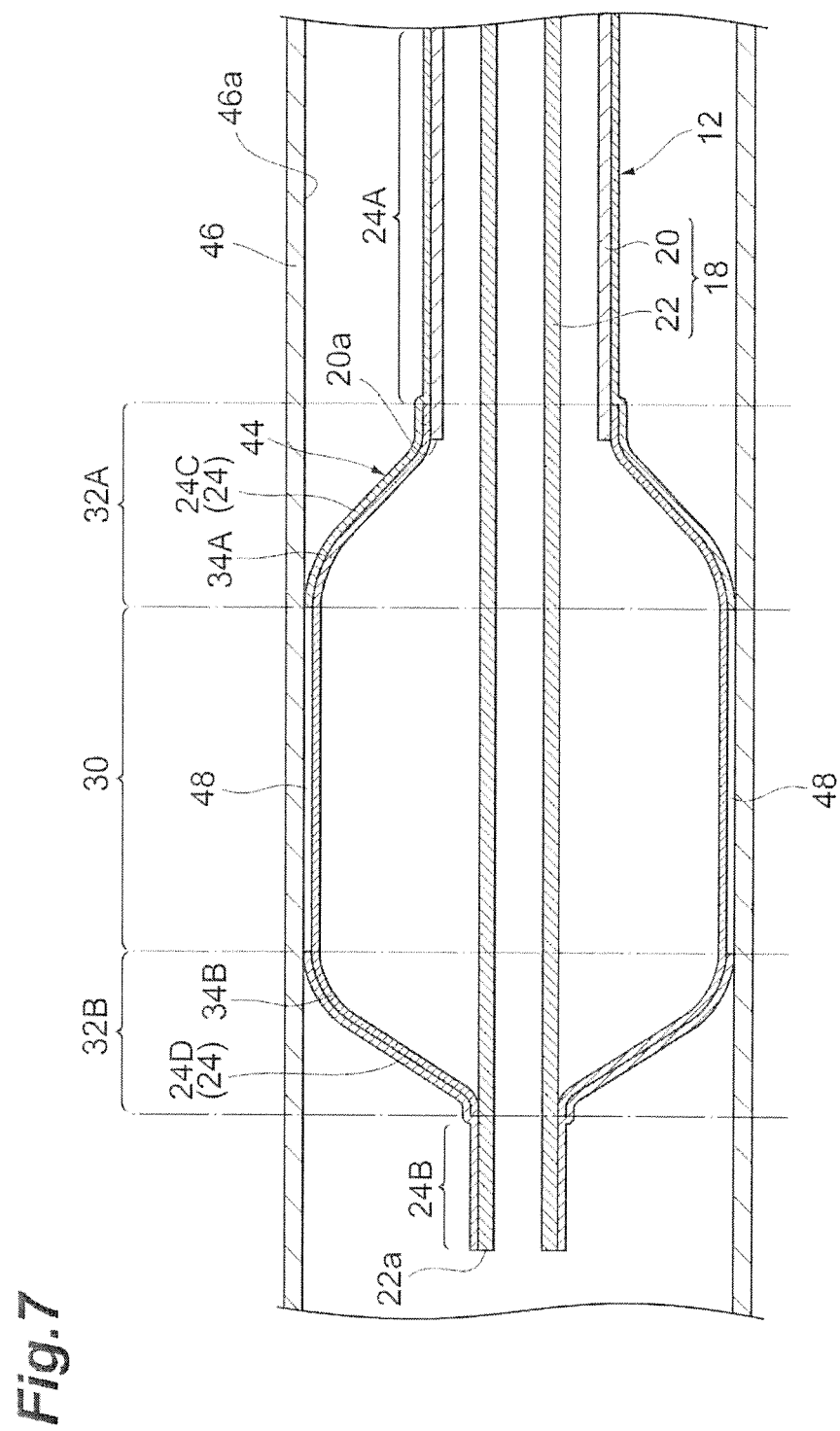
FIG. 7 is a schematic diagram illustrating a case where a blood vessel is occluded with a balloon in which a coating is provided on the whole of a first tapered portion and a second tapered portion.

FIG. 7 is a schematic diagram illustrating a state where a blood vessel 46 is occluded by a balloon 44 in which the hydrophilic coating 24 is provided on the whole of the proximal and distal tapered portions. Blood in the blood vessel 46 and a guide wire are not illustrated in FIG. 7. The balloon 44 is similar in configuration to the balloon 14 except that the hydrophilic coating 24 is provided on the whole of the proximal and distal tapered portions. Accordingly, for convenience of description, the same reference numerals will be used to refer to elements of the balloon 44 corresponding to components of the balloon 14 so that description is not repeated.

It is conceivable that, when the blood vessel 46 is to be occluded with the balloon 44, the hydrophilic coating 24 is provided on the whole of the proximal tapered portion 32A and the distal tapered portion 32B without the hydrophilic coating 24 on the straight pipe portion 30 and as in the balloon 44 illustrated in FIG. 7 so that slip of the balloon 44 is suppressed while smoothly inserting balloon catheter into the blood vessel 46.

However, the hydrophilic coating 24 comes into contact with an inner wall surface 46a of the blood vessel 46 when the balloon 44 is expanded because the hydrophilic coating 24 has thickness and becomes even thicker through expansion when the hydrophilic coating 24 comes into contact with blood after being inserted into the blood vessel 46. As a result, a weir 48 is formed by the inner wall surface 46a, the outer surface of the straight pipe portion 30 and the hydrophilic coating 24 provided on each of the proximal tapered portion 32A and the distal tapered portion 32B. Because of this weir 48, a blood layer is formed between the straight pipe portion 30 and the inner wall surface 46a when the balloon 44 is deformed from the contracted state to the expanded state thereof. Because of this liquid layer, the straight pipe portion 30 and the inner wall surface 46a are unlikely to come into contact with each other, and thus slip of the balloon 44 with respect to the inner wall surface 46a may occur.

Figure 8:
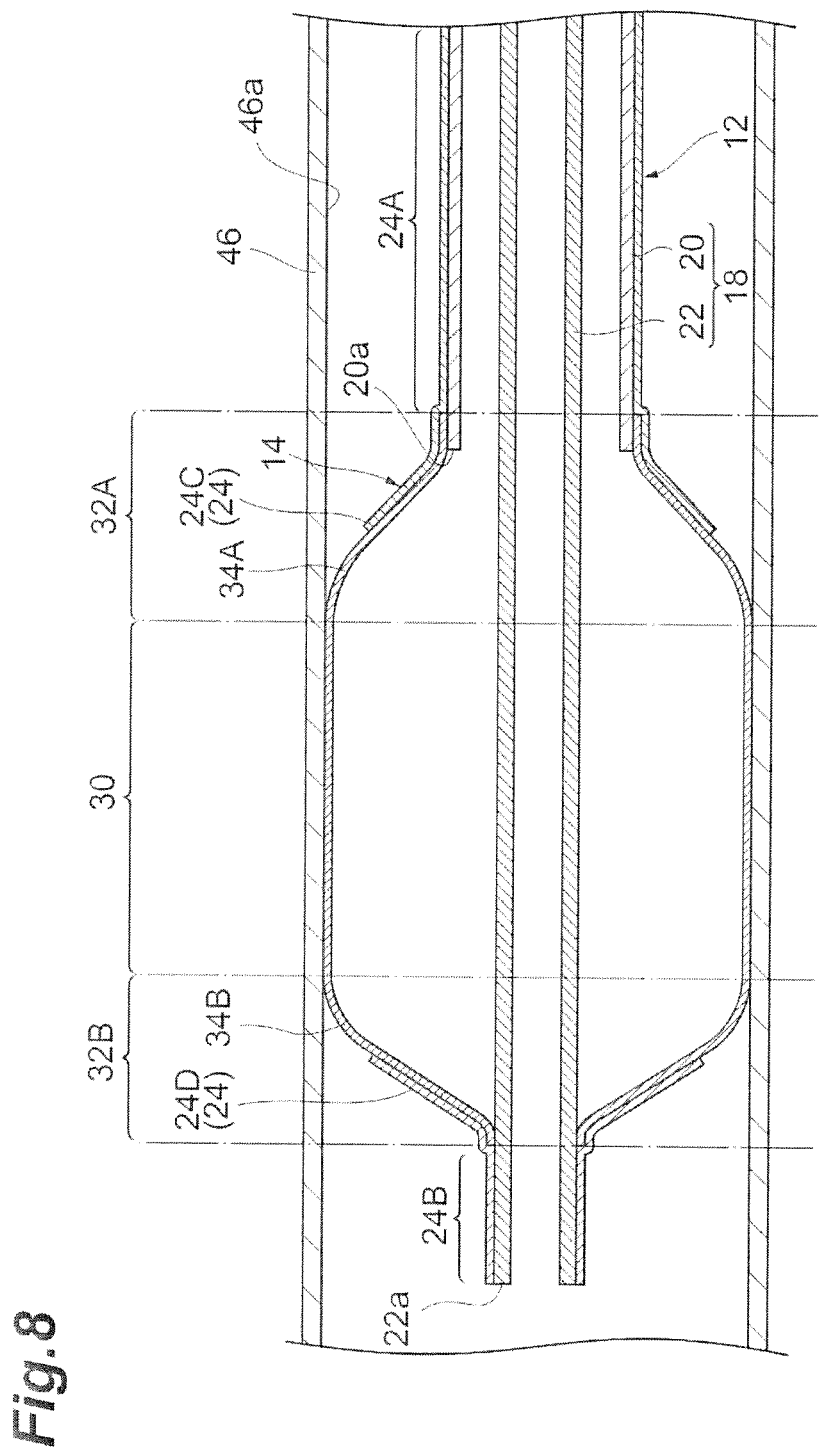
FIG. 8 is a schematic diagram illustrating a case where a blood vessel is occluded with the balloon of the balloon catheter illustrated in FIG. 1.

In the balloon 14, in contrast, the high lubrication regions 36A and 36B and the low lubrication regions 38A and 38B are provided in the proximal tapered portion 32A and the distal tapered portion 32B such that the boundaries B are on the proximal tapered portion 32A and the distal tapered portion 32B. In addition, the low lubrication regions 38A and 38B of the proximal tapered portion 32A and the distal tapered portion 32B and the low lubrication region 38C of the straight pipe portion 30 are continuous. Accordingly, as illustrated in FIG. 8, the weir 48 illustrated in FIG. 7 is not formed even when the high lubrication regions 36A and 36B have the hydrophilic coatings 24C and 24D such that the hydrophilic coatings 24C and 24D constitute the outer surfaces of the high lubrication regions 36A and 36B.

Accordingly, the blood between the straight pipe portion 30 and the inner wall surface 46a of the blood vessel 46 is discharged from the space between the straight pipe portion 30 and the inner wall surface 46a of the blood vessel 46, without being blocked by the hydrophilic coating 24 provided on the proximal tapered portion 32A and the distal tapered portion 32B, even when the balloon 14 is deformed from the contracted state to the expanded state. As a result, the straight pipe portion 30 and the inner wall surface 46a come into contact with each other in a reliable manner. Slip of the balloon 14 can be more reliably suppressed when the blood vessel 46 is occluded by the balloon 14 because the outer surface of the straight pipe portion 30 is the low lubrication region 38A. In other words, the slip resistance of the balloon 14 is improved in the balloon catheter 10.

The lubricity of the low lubrication region 38C can be any lubricity that prevents slip due to a blood flow or the like when the low lubrication region 38A is in contact with the inner wall surface 46a, and may be as low as possible. In the present embodiment, the low lubrication region is the region of the balloon main body 40 that is not coated with the hydrophilic coating 24, and thus the lubricity of the low lubrication regions 38A and 38B is also similar to the lubricity of the low lubrication region 38C.

In order to discharge the blood between the straight pipe portion 30 and the inner wall surface 46a of the blood vessel 46 during expansion of the balloon 14 as described above, it is enough that the region where the hydrophilic coating 24 is formed and the thickness of the hydrophilic coating 24 are set such that the hydrophilic coating 24 does not come into contact with the inner wall surface 46a of the blood vessel 46 in the expanded state during use of the balloon 14.

In a case where the hydrophilic coating 24 is not provided on the entire outer surface of the straight pipe portion 30 as in the present embodiment, that is, in a case where the entire outer surface of the straight pipe portion 30 is the low lubrication region 38C, slip of the balloon 14 can be further suppressed because the friction between the straight pipe portion 30 and the blood vessel 46 further increases when the straight pipe portion 30 is in contact with the blood vessel 46.

In an embodiment in which the hydrophilic coating 24 is provided on both the proximal tapered portion 32A and the distal tapered portion 32B, the blood between the straight pipe portion 30 and the inner wall surface 46a of the blood vessel 46 can be discharged from both sides of the straight pipe portion 30. Accordingly, the blood between the straight pipe portion 30 and the inner wall surface 46a can be discharged with ease, and thus slip of the balloon 14 can be further suppressed.

In an embodiment in which the hydrophilic coating 24 is provided over the entire circumferential direction in predetermined regions of the outer surfaces of the proximal tapered portion 32A and the distal tapered portion 32B, the blood between the straight pipe portion 30 and the inner wall surface 46a of the blood vessel 46 can be discharged in the entire outer circumferential direction of the straight pipe portion 30. Accordingly, the blood between the straight pipe portion 30 and the inner wall surface 46a can be removed in a more reliable manner, and thus slip of the balloon 14 can be further suppressed.

Although one or more embodiments of the present invention have been described above, the present invention is not limited to the embodiment and the modification example described above, and is indicated by the scope of the claims. It should be noted that the present invention includes every change within the meaning and range equivalent to the scope of the claims.

For example, it is enough that the low lubrication region is provided over the straight pipe portion and at least one of the first tapered portion and the second tapered portion in the balloon, at least a part of the low lubrication region is an annular-surface low lubrication region (more specifically, an annular-surface low lubrication region when the part is viewed from the long axis direction), and a surface high lubrication region is provided adjacent to the low lubrication region in predetermined tapered portion corresponding to at least one of the first tapered portion and the second tapered portion and being provided with the low lubrication region.

Accordingly, for example, the straight pipe portion may be provided with a hydrophilic coating, that is, a high lubrication region. It is unnecessary to provide the hydrophilic coating in the entire circumferential direction as long as the hydrophilic coating is a surface hydrophilic coating on the proximal tapered portion and the distal tapered portion. It is unnecessary for the direction, in which an annular-surface part of the low lubrication region provided in the balloon extends, to be orthogonal to the long axis direction C in the lateral view of the balloon as long as a part of the low lubrication region is an annular-surface low lubrication region.

Figure 9:
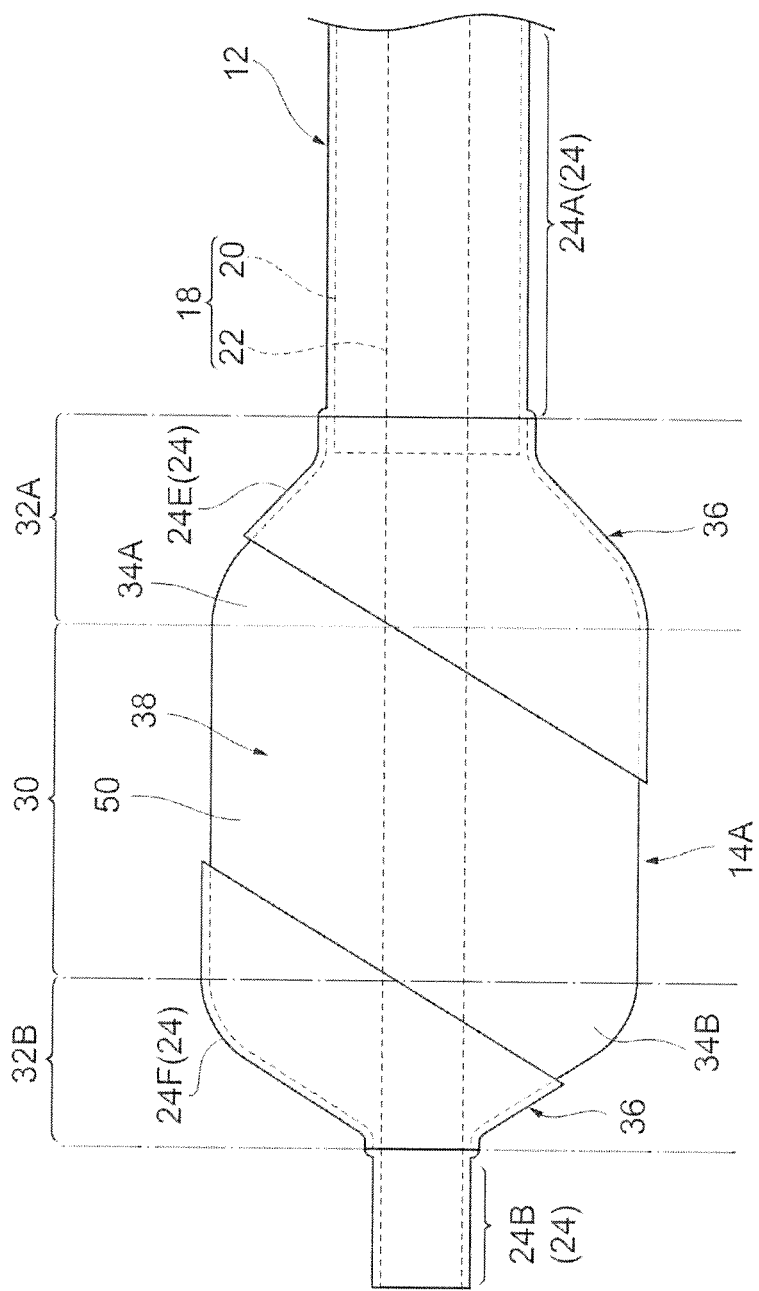
FIG. 9 is a drawing for describing a modification example of the balloon catheter.

Accordingly, for example, a balloon 14A illustrated in FIG. 9 may take the place of the balloon 14. The balloon 14A will be described below with the same reference numerals used to refer to elements corresponding to components of the balloon 14. In the description of FIG. 9, the high lubrication region will be referred to as a high lubrication region 36.

In the balloon 14A, the low lubrication region 38 is provided an annular-surface low lubrication region, obliquely extending, in the lateral view of the balloon 14A, over the proximal tapered portion (first tapered portion) 32A, the straight pipe portion 30 and the distal tapered portion (second tapered portion) 32B, and the hydrophilic coating 24 is provided as a surface hydrophilic coating on both sides thereof. In the following description, the part of the hydrophilic coating 24 on the proximal tapered portion 32A side will be referred to as a hydrophilic coating 24E and the part of the hydrophilic coating 24 on the distal tapered portion 32B side will be referred to as a hydrophilic coating 24F. Also in this embodiment, the surface high lubrication region 36 including the hydrophilic coatings 24E and 24F and adjacent to the low lubrication region 38 is provided in each of the proximal tapered portion 32A and the distal tapered portion 32B.

Accordingly, a balloon catheter that adopts the balloon 14A instead of the balloon 14 in the balloon catheter 10 illustrated in FIG. 1 is also at least similar in action and effect to the balloon catheter 10. In other words, slip resistance can be improved since the blood between the straight pipe portion 30 and the inner wall surface of a blood vessel is discharged, without being blocked, from the space between the inner wall surface of the blood vessel and the straight pipe portion 30 when the balloon 14 is expanded in the blood vessel.

The balloon 14A can be manufactured by masking the region corresponding to the low lubrication region 38, and forming the hydrophilic coating 24 on the other regions (more specifically, the hydrophilic coatings 24E and 24F) in the balloon main body comprising a straight pipe portion main body 50, the proximal tapered portion main body 34A and the distal tapered portion main body 34B. In the balloon main body, the straight pipe portion main body 50, the proximal tapered portion main body 34A, and the distal tapered portion main body 34B are regions that become the straight pipe portion 30, the proximal tapered portion 32A and the distal tapered portion 32B by the formation of the hydrophilic coatings 24E and 24F. In the balloon 14A, the entire outer surface of the straight pipe portion 30 may be a low lubrication region.

The low lubricity of the low lubrication region that is provided in each of the proximal tapered portion and the distal tapered portion and the low lubricity of the low lubrication region that is provided in the straight pipe portion may differ from each other.

In the above description, the predetermined tapered portion corresponds to both of the proximal tapered portion (first tapered portion) and the distal tapered portion (second tapered portion). In other words, the low lubrication region continuously connected from the low lubrication region provided in the straight pipe portion and the high lubrication region adjacent thereto are provided in both the proximal tapered portion and the distal tapered portion. However, either the proximal tapered portion or the distal tapered portion may be the predetermined tapered portion instead. Accordingly, for example, the entire distal tapered portion may be coated with the hydrophilic coating and the entire distal tapered portion may be a high lubrication region as long as the high lubrication region is formed adjacent to the low lubrication region and the low lubrication region continuously connected from the straight pipe portion is formed by coating a part of the proximal tapered portion with the hydrophilic coating. Even in this case, the blood between the straight pipe portion and the inner wall surface of a blood vessel can be discharged from the proximal tapered portion side.

In an embodiment in which the high lubrication region has a coating on at least the outer surface thereof, the coating constituting the outer surface of the high lubrication region may not be a hydrophilic coating as long as the coating is higher in lubricity than the low lubrication region. The high lubrication region may not be provided by a coating as long as the high lubrication region and the low lubrication region are formed in the balloon.

Although a balloon catheter for blood vessel occluding has been exemplified as the balloon catheter, one or more embodiments of the present invention are also applicable to a balloon catheter inserted into a tubular body through which a liquid flows such as a blood vessel and applied to occlusion or expansion of the tubular body.

The above-described embodiment and various modification examples can be combined in various forms within the scope of the present invention. Those skilled in the art, having benefit of this disclosure, will appreciate that various other embodiments may be devised without departing from the scope of the present invention. Accordingly, the scope of the invention should be limited only by the attached claims.

REFERENCE SIGNS LIST

10: balloon catheter, 14, 14A: balloon, 18: shaft, 24, 24A, 24B, 24C, 24D, 24E, 24F: hydrophilic coating (coating), 30: straight pipe portion (first region), 30a: proximal end (first end), 30b: distal end (second end), 32A: proximal tapered portion (first tapered portion, predetermined tapered portion), 32B: distal tapered portion (second tapered portion, predetermined tapered portion), 34A: proximal tapered portion main body (second region), 34B: distal tapered portion main body (third region), 36, 36A, 36B: high lubrication region, 38, 38A, 38B: low lubrication region, 40: balloon main body, 42: masking member, 50: straight pipe portion main body (first region), C: long axis direction.

What is claimed is:

1. A balloon catheter comprising:
    a shaft extending in one direction;
    a balloon disposed on the shaft;
    a first lubrication region;
    a second lubrication region,
    wherein the balloon in an expanded state comprises:
        a straight pipe portion;
        a first tapered portion disposed at a first end of the straight pipe portion in a long axis direction of the shaft; and
        a second tapered portion disposed at a second end of the straight pipe portion positioned opposite to the first end of the straight pipe portion in the long axis direction,
    wherein each of the first tapered portion and the second tapered portion tapers away from the straight pipe portion,
    wherein the first lubrication region extends over the straight pipe portion and the first tapered portion,
    wherein at least a part of the first lubrication region is an annular lubrication region,
    wherein the second lubrication region is provided in the first tapered portion, the second lubrication region being adjacent to the first lubrication region,
    wherein lubricity of the second lubrication region is higher than lubricity of the first lubrication region,
    wherein the annular lubrication region is located in the first tapered portion,
    wherein a boundary between the second lubrication region and the first lubrication region is orthogonal to the long axis direction in a lateral view of the balloon, and
    wherein a second length/a first length is 0.05 to 0.9, the first length being a length of the first tapered portion in the long axis direction and the second length being a length of the first lubrication region in the first tapered portion in the long axis direction.

2. The balloon catheter according to claim 1,
    wherein a coating constitutes an outer surface of the second lubrication region,
    wherein lubricity of the coating is higher than the lubricity of the first lubrication region, and
    wherein a thickness of the first lubrication region is less than a thickness of the second lubrication region in a state where the coating is swollen.

3. The balloon catheter according to claim 1, wherein an entire outer surface of the straight pipe portion is the first lubrication region.

4. The balloon catheter according to claim 1,
    wherein the first lubrication region further extends over the second tapered portion, and
    wherein the balloon catheter further comprises another second lubrication region provided in the second tapered portion, the another second lubrication region being adjacent to the first lubrication region.

5. The balloon catheter according to claim 4,
    wherein a boundary between the second lubrication region and the first lubrication region is orthogonal to the long axis direction in a lateral view of the balloon, and wherein a fourth length/a third length is 0.05 to 0.9, the third length being a length of the second tapered portion in the long axis direction and the fourth length being a length of the first lubrication region in the second tapered portion in the long axis direction.

6. The balloon catheter according to claim 1,
wherein the first lubrication region consists essentially of the annular lubrication region, the annular lubrication region obliquely extending over the first tapered portion, the straight pipe portion and the second tapered portion in a lateral view of the balloon, and
wherein each side of the first lubrication region is provided with the second lubrication region.

7. A balloon catheter comprising:
a shaft extending in one direction;
a balloon disposed on the shaft;
a first lubrication region;
a second lubrication region,
wherein the balloon in an expanded state comprises:
  a straight pipe portion;
  a first tapered portion disposed at a first end of the straight pipe portion in a long axis direction of the shaft; and
  a second tapered portion disposed at a second end of the straight pipe portion positioned opposite to the first end of the straight pipe portion in the long axis direction,
wherein each of the first tapered portion and the second tapered portion tapers away from the straight pipe portion,
wherein the first lubrication region extends over the straight pipe portion and the first tapered portion,
wherein at least a part of the first lubrication region is an annular lubrication region,
wherein the second lubrication region is provided in the first tapered portion, the second lubrication region being adjacent to the first lubrication region,
wherein lubricity of the second lubrication region is higher than lubricity of the first lubrication region,
wherein the first lubrication region further extends over the second tapered portion,
wherein the balloon catheter further comprises another second lubrication region provided in the second tapered portion, the another second lubrication region being adjacent to the first lubrication region,
wherein a boundary between the second lubrication region and the first lubrication region is orthogonal to the long axis direction in a lateral view of the balloon,
wherein a second length/a first length is 0.05 to 0.9, the first length being a length of the first tapered portion in the long axis direction and the second length being a length of the first lubrication region in the first tapered portion in the long axis direction, and
wherein a fourth length/a third length is 0.05 to 0.9, the third length being a length of the second tapered portion in the long axis direction and the fourth length being a length of the first lubrication region in the second tapered portion in the long axis direction.

* * * * *